United States Patent [19]

Fujita

[11] Patent Number: 5,047,929

[45] Date of Patent: Sep. 10, 1991

[54] METHOD FOR PROCESSING INFORMATION ON CHEMICAL REACTIONS

[75] Inventor: Shinsaku Fujita, Kanagawa, Japan

[73] Assignee: Fuji Photo Film Co., Ltd., Kanagawa, Japan

[21] Appl. No.: 236,261

[22] Filed: Aug. 25, 1988

Related U.S. Application Data

[63] Continuation of Ser. No. 903,720, Sep. 5, 1986, abandoned.

[30] Foreign Application Priority Data

Sep. 9, 1985 [JP] Japan .............................. 60-199920

[51] Int. Cl.5 .............................................. G06F 15/20
[52] U.S. Cl. ..................................... 364/497; 364/496
[58] Field of Search ........................ 364/500, 497, 496

[56] References Cited

U.S. PATENT DOCUMENTS

| | | | |
|---|---|---|---|
| 3,663,805 | 5/1972 | Carr et al. ............................ | 364/500 |
| 3,666,932 | 5/1972 | White ................................... | 364/500 |
| 3,814,916 | 6/1974 | Sweeney .............................. | 364/500 |
| 4,205,391 | 5/1980 | Iyanov et al. ..................... | 364/496 X |
| 4,473,890 | 9/1984 | Araki .................................. | 364/900 |
| 4,642,762 | 2/1987 | Fisanick ............................. | 364/300 |
| 4,982,338 | 1/1991 | Fujita ............................. | 364/496 X |

OTHER PUBLICATIONS

"Modern Approaches to Chemical Reaction Searching" pp. 202–220, Do We Still Nedd a Classification of Reactions? by G. Vladutz.

Pp. 240–256 "Compound-Oriented and Reaction Structural Languages For Reaction Data Base Management" J. E. DuBois et al.

"Classification of Reactions by Electron Shift Patterns" pp. 2–9; J. Brandy et al. Chemica Scripta.

Roger Attias, DARC Substructure Search System, J. Chem. Inf. Comput. Sci., vol. 23, #3, 1983.

Darc System Pamphlet distributed at A.C.S. meeting Aug. 1983, by Questel Inc. in Washington, D.C.

"The Description of Organic Reactions Based on Imaginary Transition Structures," *Pure and Applied Chem.*, vol. 61, No. 3, pp. 605–608 ('89), Brochure: The Essence of ITS and Connection Table Using Complex Bond Number.

Flow Charts, *Journal of Synthetic Organic Chemistry, Japan*, vol. 47, No. 5 (1989), English translation of Japanese article written by Applicant.

*Primary Examiner*—Leo P. Picard
*Assistant Examiner*—Paramita Ghosh
*Attorney, Agent, or Firm*—Sixbey, Friedman, Leedom & Ferguson

[57] ABSTRACT

A method for processing information on chemical reactions of producing at least one product from at least one starting material, the information on chemical reactions being given in the form of an imaginary transition structure (ITS) and/or a connection table of ITS, in which bonds are distinguished and classified into three categories of (1) bonds linking two nodes appearing both in the starting and product stages, (2) bonds linking two nodes appearing only in the starting stage and (3) bonds linking two nodes appearing only in the product stage, which comprises:

detecting ring structures in said imaginary transition structures and/or said connection tables; and classifying the ring structures into any type of the following five groups:

(I) a ring structure which contains one bond (2) and no bond (3), (II) a ring structure which contains two or more bonds (2) and no bond (3), (III) a ring structure which contains no bond (2) and one bond (3), (IV) a ring structure which contains no bond (2) and two or more bonds (3), and (V) a ring structure which contains one bond (2) and one bond (3).

12 Claims, 1 Drawing Sheet

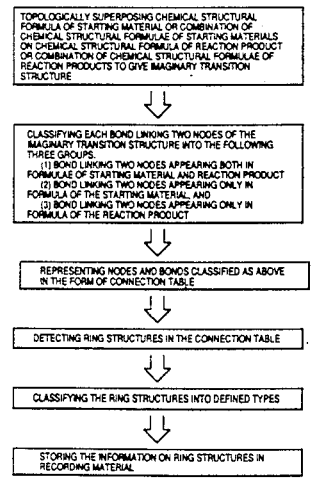

FIG. 1

TOPOLOGICALLY SUPERPOSING CHEMICAL STRUCTURAL FORMULA OF STARTING MATERIAL OR COMBINATION OF CHEMICAL STRUCTURAL FORMULAE OF STARTING MATERIALS ON CHEMICAL STRUCTURAL FORMULA OF REACTION PRODUCT OR COMBINATION OF CHEMICAL STRUCTURAL FORMULAE OF REACTION PRODUCTS TO GIVE IMAGINARY TRANSITION STRUCTURE

CLASSIFYING EACH BOND LINKING TWO NODES OF THE IMAGINARY TRANSITION STRUCTURE INTO THE FOLLOWING THREE GROUPS:
   (1) BOND LINKING TWO NODES APPEARING BOTH IN FORMULAE OF STARTING MATERIAL AND REACTION PRODUCT
   (2) BOND LINKING TWO NODES APPEARING ONLY IN FORMULA OF THE STARTING MATERIAL, AND
   (3) BOND LINKING TWO NODES APPEARING ONLY IN FORMULA OF THE REACTION PRODUCT

REPRESENTING NODES AND BONDS CLASSIFIED AS ABOVE IN THE FORM OF CONNECTION TABLE

DETECTING RING STRUCTURES IN THE CONNECTION TABLE

CLASSIFYING THE RING STRUCTURES INTO DEFINED TYPES

STORING THE INFORMATION ON RING STRUCTURES IN RECORDING MATERIAL

METHOD FOR PROCESSING INFORMATION ON CHEMICAL REACTIONS

This application is a continuation, of application Ser. No. 903,270, filed Sept. 5, 1986 now abandon.

BACKGROUNDS OF THE INVENTION

1. Field of the Invention

The present invention relates to a method for processing information on chemical reactions and more particularly, to a method for processing information on changes in the chemical structures of substances concerned with chemical reactions.

2. Description of the Prior Art

Various methods for recording structural information on chemical substances, particularly organic compounds have been proposed and attempted with the development of computers in recent years. A vast amount of organic compounds and organic reactions have been studied and worked out up to the present, and it is highly required that known chemical substances or chemical reactions are retrieved in a short time, or methods for the synthesis of new substances having the desired properties are found out, by effectively utilizing information on said known compounds and reactions. For this purpose, development of a new representation mode for chemical substances and chemical reactions is needed, which can be processed by computer (that is, which can be logically judged by computer) instead of an ordinary mode such as structural formula which can be readily treated by chemists.

Typical methods for recording chemical substances (methods for the representation or description of chemical substances) are a linear notation method such as WLN (Wiswesser Linear Notation) and a method using connection table. These methods are described in, for example, W. T. Wipke, S. R. Heller, R. J. Feldman and E. Hyde (Eds.): "Computer Representation and Manipulation of Chemical Information", John Wiley and Sons, New York, 1974. The connection table is a list in which the kind of atoms and the kinds of neighbor atoms and bonds, etc. appeared in the structural formula of chemical substance are tabulated and the connection table has an advantage that chemical substances can be retrieved atom by atom as compared with the linear notation.

Further, methods for recording information on change in the chemical structures of substances (on chemical reactions) have been proposed, but a satisfactory representation method is not developed as yet. For instance, as methods for the description of chemical reactions, there are methods using a reaction code, such as a method described in J. Valls and O. Scheiner: "Chemical Information Systems", ed. by E. Ash and E. Hyde, Ellis Horwood Limited, 1975, p. 241-258; a method described in M. A. Lobeck, Angew. Chem. Intern. Ed. Engl., 9, 578(1970); and a method described in H. J. Ziegler, J. Chem. Inf. Comput. Sci., 19, 141(1979). In these methods, a view of the representation for chemical reactions is fixed and hence, these methods have a disadvantage that any novel chemical reactions can not be described. Further, there are disadvantages that since structural information on chemical substances and information on structural changes thereof are recorded in a separate form, it is hard to make an effective information retrieval.

There are other known recording methods worked out for design of synthetic pathways of chemical substances, for instance, methods described in E. J. Corey, R. D. Cramer and W. J. Howe, J. Am. Chem. Soc., 94, 440(1972); and I. Ugi, J. Bauer, J. Braodt, J. Friedrich, J. Gasteiger, L. Jochum and W. Schubert, Angew. Chem. Intern. Ed. Engl., 18, 111(1979).

SUMMARY OF THE INVENTION

It is an object of the present invention to provide a novel processing method for extracting information on ring structures concerned with reactions from information on chemical reactions.

It is another object of the present invention to provide a processing method for recording and storing information on ring structures concerned with reactions on the basis of information on chemical reactions in a representation mode which can be processed by computer.

The present invention provides a method for processing information on chemical reactions of producing at least one product from at least one starting material, said information on chemical reactions being given in the form of an imaginary transition structure and/or a connection table containing information on nodes and bonds linking two nodes, in which bonds are distinguished between the starting material and the product topologically superposed thereon and classified into three categories of (1) bonds linking two nodes appearing both in the starting and product stages, (2) bonds linking two nodes appearing only in the starting stage and (3) bonds linking two nodes appearing only in the product stage, which comprises: detecting ring structures in said imaginary transition structures and/or said connection tables; and classifying the ring structures into any type of the following five groups:

(I) a ring structure which contains one bond (2) appearing only in the starting stage and no bond (3) appearing only in the product stage, (II) a ring structure which contains two or more bonds (2) appearing only in the starting stage and no bond (3) appearing only in the product stage, (III) a ring structure which contains no bond (2) appearing only in the starting stage and one bond (3) appearing only in the product stage, (IV) a ring structure which contains no bond (2) appearing only in the starting stage and two or more bonds (3) appearing only in the product stage, and (V) a ring structure which contains one bond (2) appearing only in the starting stage and one bond (3) appearing only in the product stage.

The present invention also provides methods for processing information on chemical reactions of producing at least one product from at least one starting material, said information on chemical reactions being given in the form of an imaginary transition structure and/or a connection table containing information on nodes and bonds linking two nodes, in which bonds are distinguished between the starting material and the product topologically superposed thereon and classified into three categories of (1) bonds linking two nodes appearing both in the starting and product stages, (2) bonds linking two nodes appearing only in the starting stage and (3) bonds linking two nodes appearing only in the product stage, wherein,

[1] a method which comprises extracting from the imaginary transition structure and/or the connection table, information on at least one ring structure composed of plural bonds (1) appearing both in the starting and product stages and one bond (2) appearing only in the starting stage;

[2] a method which comprises extracting from the imaginary transition structure and/or the connection table, information on at least one ring structure composed of one or more bonds (1) appearing both in the starting and product stages and two or more bonds (2) appearing only in the starting stage;

[3] a method which comprises extracting from the imaginary transition structure and/or the connection table, information on at least one ring structure composed of plural bonds (1) appearing both in the starting and product stages and one bond (3) appearing only in the product stage;

[4] a method which comprises extracting from the imaginary transition structure and/or the connection table, information on at least one ring structure composed of one or more bonds (1) appearing both in the starting and product stages and two or more bonds (3) appearing only in the product stage; and

[5] a method which comprises extracting from the imaginary transition structure and/or the connection table, information on at least one ring structure composed of one or more bonds (1) appearing both in the starting and product stages, one bond (2) appearing only in the starting stage and one bond (3) appearing only in the product stage.

According to the present invention, chemical reactions can be classified based on bond changes inherent to the reactions, i.e., ring structures concerned with the reactions, and further information on said ring structures can be automatically obtained, by subjecting information on the chemical reactions inputted in the form of imaginary transition structure and/or connection table to appropriate processing.

The term "imaginary transition structure" (hereinafter referred to as ITS) used herein refers to two-dimensional or three-dimensional structural diagram (graph) wherein changes in the structure of substances concerned with a chemical reaction are represented by distinguishing bonds linking two adjacent nodes and classifying them into three categories of (1) bonds linking two adjacent nodes appearing only in the starting stage, (2) bonds linking two adjacent nodes appearing only in the product stage and (3) bonds linking two adjacent nodes appearing both in the starting and product stages. By using this structural diagram, the chemical reaction can be described by a form which is visually acceptable and readily comprehensible to chemists and technologists in accordance with ordinary structural formula of chemical substance or three-dimensional form thereof.

Connection table of ITS (hereinafter simply referred to as "connection table") is a table which essentially consists of a combination of the kind of nodes and the kinds of neighboring nodes and bonds linking these two nodes in a chemical reaction, being simple and understandable. By using this connection table, information on chemical reactions can be stored in a recording medium without requiring so large capacity.

According to said imaginary transition structure and connection table, a chemical reaction can be basically described by a simple representation of nodes comprising atoms, groups, etc. and bonds linking two adjacent nodes. The bonds linking two nodes in the reaction system are distinguished and classified into said three categories. Therefore, when the imaginary transition structure or the connection table is subjected to simple graphic processing or appropriate operational processing depending upon the distinction of bonds applied thereto, bond changes inherent to a chemical reaction, i.e., ring structure concerned with the reaction can be detected and the chemical reaction can be classified by kinds of ring structures.

In the present invention, the term "ring structure" concerned with a chemical reaction used herein means ring structures in ring opening reactions, ring closure reactions, etc. (The ring structure appearing in ITS's may be called ITS rings.) This representation which allows that various chemical reactions are classified based on the occurrence or not of ring formation is of great value for retrieving, studying or applying individual chemical reactions or a series of chemical reactions, particularly in organic synthesis reactions where steric hindrance, reaction potential, electronegativity, etc. should be taken into consideration.

Further, not only a ring structure(s) can be detected in a chemical reaction, but also the detected ring structure can be extracted by itself and represented simply by a diagram, etc.

When information on ring structures concerned with chemical reactions is obtained in the form of a two-dimensional or three-dimensional diagram in accordance with the imaginary transition structure, there are advantages that the information is visually acceptable and can be directly used in the practical field, because the obtained form is almost the same as the ordinary representation mode of chemical substances. When information on ring structures is obtained in the form of a connection table, there are other advantages that comparison and collation with the reaction information denoted by the same form is easy and the information can be stored in a computer without requiring a large capacity.

Information on ring structures can be also represented in the form of characters, symbols or a combination thereof such as character string. The information on ring structures is denoted very simply. Accordingly, such a representation mode has advantages in that the information can be stored in a computer without requiring a large capacity and the retrieval of chemical reactions can be easily made in a short time on the basis of the stored information. It is also possible to store, record and display the information on ring structures denoted by character string, etc. in a combination with the reaction information denoted by the imaginary transition structure, connection table, etc. or with the substance information concerned with reactions, and such a combination mode is very effective in the computer processing of chemical information.

Diagrams, connection tables and/or character strings, etc. with respect to the information on ring structures can be registered (entered) and stored in a computer, recorded on a paper, or displayed on a screen such as CRT.

Further, arbitrary transformation between the two-dimensional or three-dimensional diagram and the connection table of the ring structure is possible so as to denote the information on ring structures in any form, when the connection table contains information on space coordinate of each node. By using the registered diagrams, connection tables and/or character strings, etc., chemical reactions can be retrieved and collated atom by atom. Especially, the registration of the information on ring structure in the form of the connection table or the character string makes information processing by a computer easy and makes the registration of chemical reactions in a recording medium simple, so that the storing and the management of the information can be readily conducted.

Therefore, the information retrieval of chemical reactions and chemical substances concerned therewith can be made effectively and in a short time on the basis of the stored information on ring structures, so that the time required for the collection of information on studies and investigations can be shortened, the amount of information can be increased and efficient researches can be achieved.

Furthermore, the combination of the information on ring structures obtained by the method of the present invention with the already inputted reaction information and further with the substance information obtained from the reaction information, can be effectively applied to the fields of structural analysis of chemical substances, molecular modeling and heuristic analysis of organic synthesis, all of which are highly demanded by workers concerned with the manufacture of medicines. Further, retrieval of substructures of chemical substances, correlation between structure and activity, design of synthetic pathways, automatic determination of the chemical structures of unknown compounds, mechanistic evaluation for the reaction of complicated compounds under certain conditions and prediction of mechanism therefor can be made within a practically possible range in a short time.

BRIEF DESCRIPTION OF DRAWING

FIG. 1 illustrates a flow sheet for performing the method of the present invention.

CONSTITUTION OF THE INVENTION

In the method for processing information on chemical reactions according to the present invention, ring structures concerned with chemical reactions are detected from the reaction information recorded and stored in the form of an imaginary transition structure and/or a connection table wherein bonds linking two nodes are distinguished and classified into three categories, i.e., bonds appearing only in the starting stage, bonds appearing only in the product stage and bonds appearing both in the starting and product stages, and the ring structures are classified depending upon the distinction of bonds contained therein, whereby individual reactions can be classified by said ring structures.

Further, specific ring structures are extracted from the imaginary transition structures and/or the connection tables of reactions to obtain the ring structures in the form of a diagram, a connection table and/or a character string, etc.

In the present invention, the ring structures concerned with chemical reactions are classified into five groups. Now, methods for extracting said five groups of ring structures from information on chemical reactions will be respectively described by referring to embodiments.

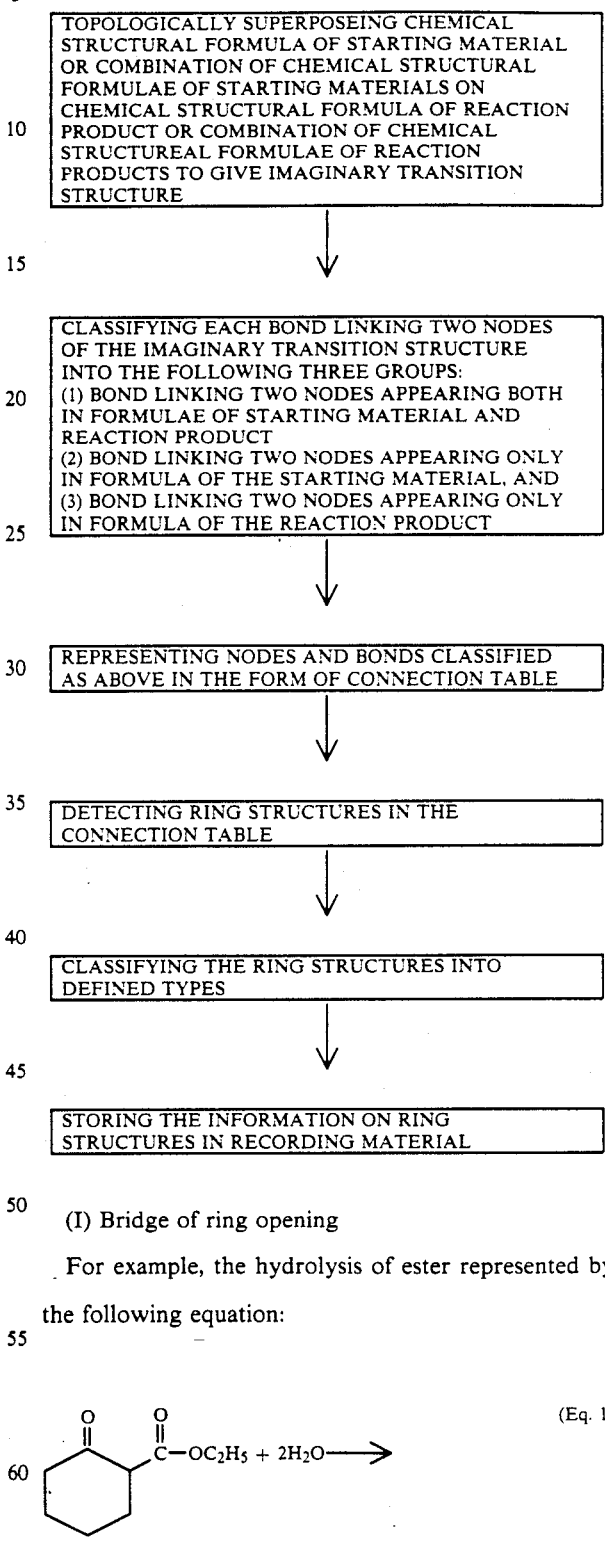

FIG. 1

(I) Bridge of ring opening

For example, the hydrolysis of ester represented by the following equation:

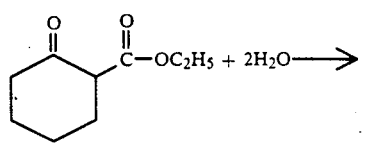

(Eq. 1)

is denoted by an imaginary transition structure (ITS):

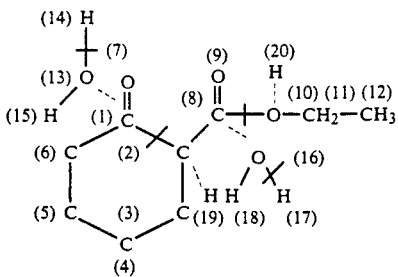

(ITS 1)

wherein
(i) the symbol — indicates bonds appearing both in the starting and product stage,
(ii) the symbol ⊥ indicates bonds appearing only in the starting stage, and
(iii) the symbol · · · indicates bonds appearing only in the product stage.

Namely, the ITS is a diagram of two-dimension or three-dimension where bonds linking two adjacent nodes are distinguished between the starting materials and the products topologically superposed thereon and classified into said three categories (i) to (iii). The term "topologically superpose" used herein means that the chemical structures of the starting materials are combined with those of the products in such a manner that the nodes appearing in the former coincide with those appearing in the latter.

In the present invention, nodes of the substances concerned with a chemical reaction are allowed to be individual atoms contained in the starting and product stages, or groups such as functional groups, for example, methyl group [node (12)], methylene group [node (11)], etc. Part of nodes appearing in the starting and product stages may be omitted in representing the chemical reaction, and the invention is not restricted by the way of decision of nodes.

In the imaginary transition structure (ITS) according to the present invention, the notation for distinguishing the three kinds of bonds is by no means limited to the symbols defined by the above (i) to (iii), but the notation may be done by any means, for example: characters such as numerals (1, 2, 3, . . . ), colors (black, red, green, etc.), so long as users can judge the notation through the senses and it can be processed by computer.

In the invention hereinafter, (i) bonds (symbol —) appearing both in the starting and product stages are referred to as colorless bonds or "par-bonds",
(ii) bonds (symbol ⊥) appearing only in the starting stage are referred to as "out-bonds", and
(iii) bonds (symbol · · ·) appearing only in the product stage are referred to as "in-bonds".

Further, the out- and in-bonds are together referred to as colored bond and all the bonds appeared in ITS (par-, out- and in-bonds) are referred to as "ITS bonds" or imaginary bonds.

The types of bonds appearing in the imaginary transition structure are shown in Table 1, wherein the numerical value in the horizontal means a characteristic of in-and-out.

TABLE 1

| Characteristic of In-and-out | −3 | −2 | −1 | 0 | +1 | +2 | +3 |
|---|---|---|---|---|---|---|---|
| Single Bond | | | (1 − 1) | (1 + 0) | (0 + 1) | | |
| Double Bond | | (2 − 2) | (2 − 1) | (2 + 0) | (1 + 1) | (0 + 2) | |
| Triple Bond | (3 − 3) | (3 − 2) | (3 − 1) | (3 + 0) | (2 + 1) | (1 + 2) | (0 + 3) |

In Table 1, a bond represented by the symbol is a single in-bond and denoted by a pair of integers (0+1) where 0 indicates that no bond is in the starting stage before reaction and +1 indicates that a bond is singly formed in the product stage after reaction. Similarly, a bond represented by the symbol ⊥ is a single out-bond and denoted by a pair of integers (1−1), which means that a single bond in the starting stage before reaction is cleaved (to disappear) in the product stage after reaction. A bond represented by a pair of integers (2−1) is a double bond singly cleaved and denoted by the symbol .

In this way, the kinds of bonds can be denoted by a pair of integers (a,b) wherein the integer a is bond multiplicity of the corresponding bond of the starting material and the integer b is difference in the bond multiplicity between the product and the starting material, which is referred to as "complex bond number" or "imaginary multiplicity". Even when the bond multiplicity is two or more, it can be simply denoted. If desired, the comma (,) of (a,b) may be deleted. This notation does not need large storage capacity and can be directly processed by computer, so that the notation is particularly preferred in the storage of data on chemical reactions.

Alternatively, chemical reactions are denoted by a connection table of ITS containing information on nodes, neighbor nodes and bonds linking said two nodes according to ITS.

Table 2 shows a connection table of the hydrolysis reaction of ester (Eq. 1).

As shown in Table 2, the connection table is a table in which all nodes, all nodes neighboring on each node and the kinds of bonds linking two adjacent nodes are listed in order of node's number with respect to the starting stage (2-ethoxycarbonyl cyclohexanon and water) and the product stage (pimelic acid and ethanol) concerned with the reaction.

TABLE 2

| Node No. | Kind | Neighbor 1 Node (a, b) | Neighbor 2 Node (a, b) | Neighbor 3 Node (a, b) | Neighbor 4 Node (a, b) |
|---|---|---|---|---|---|
| 1 | C | 2 (1 − 1) | 6 (1 + 0) | 7 (2 + 0) | 13 (0 + 1) |
| 2 | C | 1 (1 − 1) | 3 (1 + 0) | 8 (1 + 0) | 19 (0 + 1) |
| 3 | C | 2 (1 + 0) | 4 (1 + 0) | | |
| 4 | C | 3 (1 + 0) | 5 (1 + 0) | | |
| 5 | C | 4 (1 + 0) | 6 (1 + 0) | | |
| 6 | C | 1 (1 + 0) | 5 (1 + 0) | | |
| 7 | O | 1 (2 + 0) | | | |
| 8 | C | 2 (1 + 0) | 9 (2 + 0) | 10 (1 − 1) | 16 (0 + 1) |
| 9 | O | 8 (2 + 0) | | | |
| 10 | O | 8 (1 − 1) | 11 (1 + 0) | 20 (0 + 1) | |
| 11 | CH$_2$ | 10 (1 + 0) | 12 (1 + 0) | | |
| 12 | CH$_3$ | 11 (1 + 0) | | | |
| 13 | O | 1 (0 + 1) | 14 (1 − 1) | 15 (1 + 0) | |
| 14 | H | 13 (1 − 1) | | | |
| 15 | H | 13 (1 + 0) | | | |
| 16 | O | 8 (0 + 1) | 17 (1 − 1) | 18 (1 + 0) | |
| 17 | H | 16 (1 − 1) | | | |
| 18 | H | 16 (1 + 0) | | | |
| 19 | H | 2 (0 + 1) | | | |
| 20 | H | 10 (0 + 1) | | | |

The connection table may be prepared from the imaginary transition structure. On the contrary, when the connection table contains information on the space coordinate of each node, the imaginary transition structure can be prepared therefrom. In other words, the imaginary transition structure and the connection table are in the relation of inside and outside of one registration and representation mode of reaction information.

The information on the space coordinates of nodes may be incorporated in the connection table as described above. Further, information on stereochemistry and electronic charges of nodes; information on spectral and physical properties of substances related to chemical reactions; and information on reaction enthalpy, reaction temperature, reaction time, catalysts, reaction atmosphere, reaction media, yields, by-products, etc. may be combined to the imaginary transition structure and/or the connection table, if desired. Further, the imaginary transition structures and/or connection tables may be numbered one by one or reaction names may be registered together with them in order to facilitate the storage, management and retrieval of the reaction information.

Information on ring structure concerned with the reaction is obtained from the imaginary transition structure (ITS 1) of the hydrolysis of ester in the following manner.

A part where nodes are connected with some of all colorless and colored bonds in ITS 1 to form a looped string is perceived and detected.

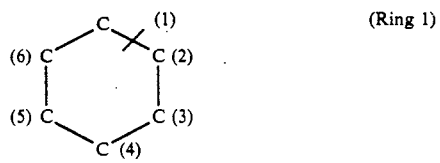

(Ring 1)

The perception of ring structure for ITS can be made, for instance, by using methods described in the literatures: A. Zamora, J. Chem. Inf. Comp. Sci., 16, 40(1976); E. J. Corey, G. A. Peterson, J. Am. Chem. Soc., 94, 460(1972); and S. B. Elk, J. Chem. Inf. Comp. Sci., 25, 11(1985).

The resulting ring structure (Ring 1) contains only one out-band and the rest of bonds is colorless. Such ring structure is referred to as "bridge of ring opening" (or "ring of ring opening"). The bridge of ring opening appears in reactions wherein one of bonds constituting a ring present in the starting material is cleaved. This ring structure corresponds to such a ring opening reaction as represented by Eq. 1 and is specific thereto.

The ring structure concerned with a chemical reaction, i.e., ring strucutre appear in ITS shows representation inherent to the reaction and is an important factor in the retrieval of chemical reactions.

The ring structure is obtained in the form of a two-dimensional or three-dimensional diagram, depending upon whether ITS is of two-dimension or of three-dimension.

Thus, the information processing of the invention is conducted on the basis of ITS to obtain information on ring structures in the form of a diagram (i.e., in a two-dimensional or three-dimensional form), said diagram being visually acceptable and readily comprehensible to chemists who intend to utilize the obtained information.

The ring structure is also represented in the form of characters, symbols or a combination thereof. For example, when the diagram as shown above is simplified to denote each node with node's number and to line up the numbers, Ring 1 is represented by the following character string:

Ring 1: (1) (2) (3) (4) (5) (6) (1)

The ring structure represented by such a character string is easy to enter and store in a computer, and the computer processing based on said ring structure such as the information retrieval is made easy. Such a representation mode may be used as additional information to the reaction information represented by another form owing to not requiring a large capacity for storage.

Alternatively, information on the bridge of ring opening can be directly extracted from a connection table of reaction. There is detected a plurality of bonds (bond group) which consist of one out-bond and two or more colorless bonds and with which nodes are connected to form a looped string, among all of colorless and colored bonds appeared in the connection table. The bonds are then arranged in such a manner that the node's numbers make sequence to obtain the information on a ring structure.

For instance, when bonds linking two nodes are denoted by a pair of integers (a,b), wherein the integer a is bond multiplicity of the corresponding bond of the starting material and the integer b is the difference in the bond multiplicity between the product and the starting material, as shown in Table 2, all bonds in the connection table satisfy the condition of either $a \neq 0$ or $b \neq 0$, and all of the colorless and colored bonds satisfy the following conditions, respectively.

(i) colorless bond:
  $a \neq 0$
  $a + b \neq 0$
(ii) out-bond:
  $a \neq 0$  $b = 0$
  $a + b = 0$
(iii) in-bond:
  $a = 0$  $b \neq 0$
  $a + b \neq 0$ Accordingly, the information on the bridge of ring opening can be obtained as follows: A set of (a,b) is detected in Table 2, which is the bond group wherein node's numbers thereof are sequential to form a loop and is composed of one (a,b) satisfying the condition of a+b+0 and other (a,b) satisfying the condition of a≠0 and a+b≠0. After the detection, a connection table which comprises the set of (a,b) arranged so that the node's numbers concerned with these (a,b) make sequence is newly prepared.

The obtained connection table of ring structure for the hydrolysis of ester is shown in Table 3.

TABLE 3

| Bond | (a, b) | a + b | a ≠ 0, a + b ≠ 0 | a + b = 0 | a = 0 |
|---|---|---|---|---|---|
| (1) (2) | (1 − 1) | 1 | — | 1 | — |
| (2) (3) | (1 + 0) | 1 | 1 | — | — |
| (3) (4) | (1 + 0) | 1 | 1 | — | — |
| (4) (5) | (1 + 0) | 1 | 1 | — | — |
| (5) (6) | (1 + 0) | 1 | 1 | — | — |
| (6) (1) | (1 + 0) | 1 | 1 | — | — |
| Total | | | 5 | 1 | 0 |

According to the information processing of the invention on the basis of the connection table, computer processing can be directly conducted thereof and information on ring structures can be obtained simply in a short time. Further, the obtained information can be recorded and stored without requiring a large capacity.

The ring structure is also simply represented by the above-described character string by transforming it from the obtained connection table. Further, when the connection table of ring structure contains information on space coordinate of each node, transformation between the diagram and the connection table of ring structure is made arbitrarilly so that the ring structure can be represented by any form. A diagram of ring structure is obtained, for instance by conducting the extraction of ring structure from the connection table of reaction and then transforming the newly obtained connection table into a diagram.

(II) Bridge of ring cleavage

For example, a reaction represented by the following equation:

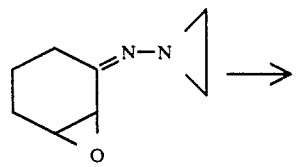

(Eq. 2)

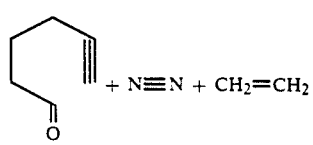

is denoted by an imaginary transition structure (ITS).

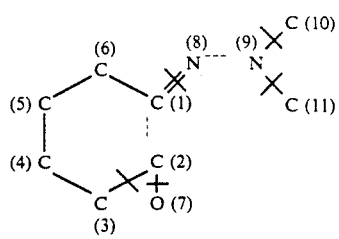

(ITS 2)

When ITS 2 is subjected to the above-described processing to extract ring structures and to represent them with character strings, at least the following three ring structures are obtained.

Ring 2a: (9) (10) (11) (9)
Ring 2b: (2) (3) (7) (2)
Ring 2c: (1) (2) (3) (4) (5) (6) (1)

When a connection table corresponding to ITS 2 is subjected to the processing of extracting ring structure (i.e. extracting a set of (a,b) where nodes are connected with bonds to form a loop), connection tables of ring structures are obtained. The connection tables of Rings 2a and 2b are shown in Table 4.

TABLE 4

| Bond | (a, b) | a + b | a ≠ 0, a + b ≠ 0 | a + b = 0 | a = 0 |
|---|---|---|---|---|---|
| (9) (10) | (1 − 1) | 0 | — | 1 | — |
| (10) (11) | (1 + 1) | 2 | 1 | — | — |
| (11) (9) | (2 − 1) | 0 | — | 1 | — |
| Total | | | 1 | 2 | 0 |
| (2) (3) | (1 − 1) | 0 | — | 1 | — |
| (3) (7) | (1 + 1) | 2 | 1 | — | — |
| (7) (2) | (1 − 1) | 0 | — | 1 | — |
| Total | | | 1 | 2 | 0 |

As shown in Table 4, each of Rings 2a and 2b is a three-membered ring composed of two out-bonds and one colorless bond. Such a ring structure where two or more bonds are out-bonds and all other bonds are colorless bonds is referred to as "bridge of ring cleavage". The bridge of ring cleavage appears in reactions wherein at least two of bonds constituting a ring prevent in the starting material are cleaved. Particularly, Ring 2a [(9) (10) (11) (9)] corresponds to the cleavage of an aziridine ring. Ring 2c is a bridge of ring opening.

(III) Bridge of ring closure

For instance, a chemical reaction represented by the following equation:

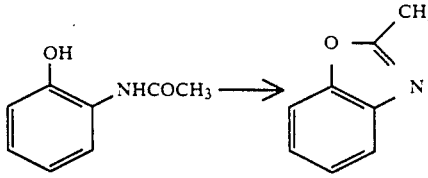

(Eq. 3)

is denoted by an imaginary transition structure (ITS).

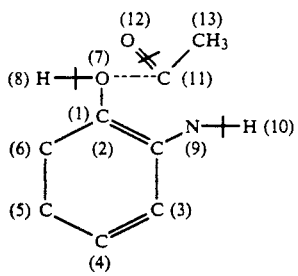
(ITS 3)

When ITS 3 is subjected to the processing of extracting ring structure, the following ring structure denoted by a character string is obtained.

Ring 3: (1) (2) (9) (11) (7) (1)

When a connection table corresponding to ITS 3 is subjected to the processing of extracting ring structure, a connection table of the ring structure (Ring 3) is obtained as shown in Table 5.

TABLE 5

| Bond | (a, b) | a + b | $a \neq 0$ a + b ≠ 0 | a + b = 0 | a = 0 |
|---|---|---|---|---|---|
| (1) (2) | (2 + 0) | 2 | 1 | — | — |
| (2) (9) | (1 + 0) | 1 | 1 | — | — |
| (9) (11) | (1 + 1) | 2 | 1 | — | — |
| (11) (7) | (0 + 1) | 1 | — | — | 1 |
| (7) (1) | (1 + 0) | 1 | 1 | — | — |
| Total | | | 4 | 0 | 1 |

As shown in Table 5, Ring 3 is a five-membered ring containing only one in-bond. Such a ring structure where one bond is in-bond and all other bonds are colorless bonds is referred to as "bridge of ring closure". The bridge of ring closure appears in reactions wherein a bond is newly formed to produce a ring in the product. This ring structure corresponds to such a ring closure reaction as represented by Eq. 3.

(VI) Bridge of ring formation

For instance, Diels-Alder reaction represented by the following equation:

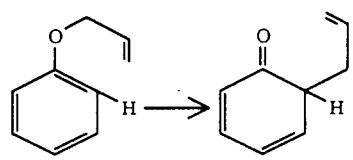
(Eq. 4)

is denoted by an imaginary transition structure (ITS).

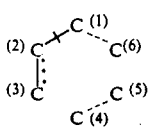
(ITS 4)

When ITS 4 is subjected to the processing of extracting ring structure, the following ring structure denoted by a character string is obtained.

Ring 4: (1) (2) (3) (4) (5) (6) (1)

When a connection table corresponding to ITS 4 is subjected to the processing of extracting ring structure, a connection table of the ring structure (Ring 4) is obtained as shown in Table 6.

TABLE 6

| Bond | (a, b) | a + b | $a \neq 0$ a + b ≠ 0 | a + b = 0 | a = 0 |
|---|---|---|---|---|---|
| (1) (2) | (2 − 1) | 1 | 1 | — | — |
| (2) (3) | (1 + 1) | 2 | 1 | — | — |
| (3) (4) | (2 − 1) | 1 | 1 | — | — |
| (4) (5) | (0 + 1) | 1 | — | — | 1 |
| (5) (6) | (2 − 1) | 1 | 1 | — | — |
| (6) (1) | (0 + 1) | 1 | — | — | 1 |
| Total | | | 4 | 0 | 2 |

As shown in Table 6, Ring 4, is a six-membered ring containing two in-bonds. Such a ring structure where two or more bonds are in-bonds and all other bonds are colorless bonds is referred to as "bridge of ring formation". The bridge of ring formation appears in reactions wherein at least two bonds are newly formed to produce a ring in the product.

(V) Ring of rearrangement

For instance, Claisen rearrangement reaction represented by the following equation

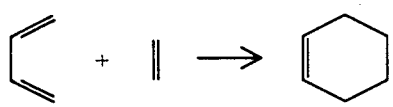
(Eq. 5)

is denoted by an imaginary transition structure (ITS).

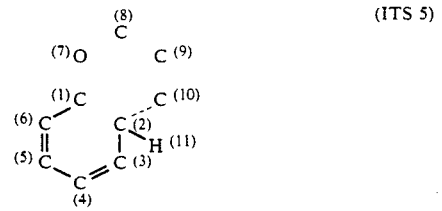
(ITS 5)

When ITS 5 is subjected to the processing of extracting ring structure, the following ring structure denoted by a character string is obtained.

Ring 5: (1) (2) (10) (9) (8) (7) (1)

When a connection table corresponding to ITS 5 is subjected to the processing of extracting ring structure, a connection table of the ring structure (Ring 5) is obtained as shown in Table 7.

TABLE 7

| Bond | (a, b) | a + b | $a \neq 0$ a + b ≠ 0 | a + b = 0 | a = 0 |
|---|---|---|---|---|---|
| (1) (2) | (2 − 1) | 1 | 1 | — | — |
| (2) (10) | (0 + 1) | 1 | — | — | 1 |
| (10) (9) | (2 − 1) | 1 | 1 | — | — |
| (9) (8) | (1 + 1) | 2 | 1 | — | — |
| (8) (7) | (1 − 1) | 0 | 0 | 1 | — |
| (7) (1) | (1 + 1) | 2 | 1 | — | — |
| Total | | | 4 | 1 | 1 |

As shown in Table 7, Ring 5 is a six-membered ring containing only one in-bond and only one out-bond. Such a ring structure where one bond is in-bond, one bond is out-bond and all other bonds are colorless bonds is referred to as "bridge of rearrangement". The bridge of rearrangement appears in reactions wherein one bond is cleaved and at the same time, one bond is newly formed at another position by movement of atoms or atomic groups to produce an intramolecular rearrangement. This ring structure corresponds to such a rearrangement reaction as represented by Eq. 5.

Both of the above-described Diels-Alder reaction (Eq. 4) and Claisen rearrangement reaction (Eq. 5) have a reaction string of a six-membered ring (which comprises nodes connected with alternate out-bonds and in-bonds and represents bond changes inherent to a chemical reaction) as shown in ITS 4 and ITS 5. In the invention, these reactions can be clearly distinguished from each other by introducing the concepts of "bridge of ring formation" and "bridge of rearrangement".

Accordingly, it is clear that the information on ring structures obtained by the present invention is very effective in the classification and the retrieval of chemical reactions. It is also clear that the representation mode of reactions used in the invention (i.e. ITS and/or connection table of ITS) is very superior to the conventional modes wherein reactions are represented by bond matrix (e.g. method by Ugi et. al.), etc.

The diagrams, connection tables and/or character strings, etc. of varius ring structures may be stored (entered) in a computer independently or additionally to ITS's or connection tables of reactions, or may be recorded or displayed through an appropriate recording or display means.

The entry in a computer may be done by storing them in main storage thereof or in an appropriate recording medium (magnetic disk, optical disk or magnetic tape). The recording may be done on a recording medium such as plain paper by an appropriate recording device, and the display may be done on a color CRT connected to a computer or an electronic equipment.

The registration and display of the information on ring structures may be done in a combination of diagram, connection table and character string, etc., and the information can be stored, recorded or displayed as additional information to the reaction information.

The information on the space coordinates of nodes may be incorporated in the connection table of ring structure. Further, information on stereochemistry and electronic charges of nodes; information on spectral and physical properties of substances related to chemical reactions; information on reaction enthalpy, reaction temperature, reaction time, catalyst, reaction atmosphere, reaction media, yields, by-products, etc. may be combined with the diagram, the connection table and/or the character string of ring structure, if desired.

In entering the diagrams, the connection tables and/or the character strings of ring structures in a computer, they may be numbered one by one or reaction names may be registered together with them in order to facilitate the storage, management and retrieval of the information on ring structures.

When the information on ring structures stored in the computer contains these additional information, the information can be widely used as data base in the fields of structure search system, reaction search system and design of organic synthesis pathways. Further, multistep reactions them. Namely, not only individual reactions but also the whole of complicated reaction pathways such as those in the organic synthesis can be simply denoted, or a part of these reactions can be extracted therefrom and denoted.

Furthermore, the use of a combination of the information on ring structure obtained by the present invention with the already inputted reaction information or the substance information can bring about the further application to the various fields of chemistry utilizing computer such as the molecular modeling according to the specific properties of substances, the design of synthetic pathways of organic compounds and the determination of structures of unknown compounds.

The processing methods for obtaining information on substances (starting materials and products) concerned with reaction from ITS's and/or connection table of reaction and for obtaining information on bond changes (reaction strings) inherent to reactions are described in more detail in our co-pending Japanese Patent Applications No. 60(1985)-185386 filed on Aug. 22, 1985 and No. 60(1985)-197463 filed on Sept. 5, 1985, respectively.

Now, a method for classifying ring structures according to the present invention will be described in more detail.

Ring structure are perceived and detected from the imaginary transition structures or the connection tables of reactions as described above. When each bond linking two nodes is denoted by a pair of integers (a,b), all bonds constituting the ring structure are classified into any of:

(i) bond having (a,b) of $a \neq 0$ and $a+b \neq 0$ (colorless bond), (ii) bond having (a,b) of $a+b=0$ (out-bond), and (iii) bond having (a,b) of $a=0$ (in-bond).

Subequently, the number of bonds belonging to each of the groups (i) to (iii) is calculated.

Depending on a combination of the individual numbers of three groups of bonds, the ring structures can be classified into six categories as shown in Table 8. In Table 8, a ring structure is a n-membered ring, wherein n is a positive integer and m is a positive integer within the range of $2 \leq m < n$.

TABLE 8

| Ring Structure | $a \neq 0$ $a + b \neq 0$ | $a + b = 0$ | $a = 0$ |
|---|---|---|---|
| I | n-1 | 1 | 0 |
| II | n-m | m | 0 |
| III | n-1 | 0 | 1 |
| IV | n-m | 0 | m |
| V | n-2 | 1 | 1 |
| VI | n | 0 | 0 |

Each of the above cases I to V corresponds to the aforementioned ring structure as follows:

I: bridge of ring opening
II: bridge of ring cleavage
III: bridge of ring closure
IV: bridge of ring formation
V: bridge of rearrangement The case VI corresponds a ring structure where all bonds are colorless bonds and means that a ring exists unchanged both in the starting and product stages, i.e., the ring structure is not concerned with the reaction.

In this way, the ring structures concerned with chemical reactions can be classified into said five categories. The above-description refers to the case where the reaction information is represented by the connection table with the notation of (a,b), but the method of the present invention is by no means limited to the case using the notation of (a,b) and applied to any connection tables and any imaginary transition structures, so long as bond changes in reactions are represented by the colorless and colored bonds (out-bond and in-bond).

Information on the classification of ring structures may be stored in a computer, or may be recorded or displayed by use of an appropriate means.

Chemical reaction can be properly classified according to the information on the classified ring structures. The retrieval of the chemical reactions can be made more effectively on the basis of the registered information on the classified ring structures. Further, the information can be used directly in the fields of the design of organic synthesis system and the molecular modeling system.

The following examples will further illustrate the method for processing information on chemical reactions according to the present invention.

EXAMPLE 1

Beckmann Rearrangement

The reaction is represented by the schematic equation.

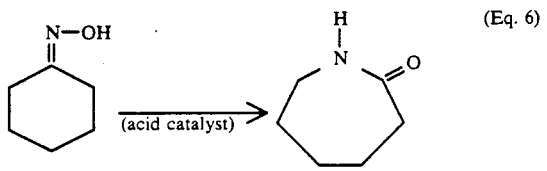 (Eq. 6)

The Beckmann rearrangement is denoted by the following imaginary transition structure.

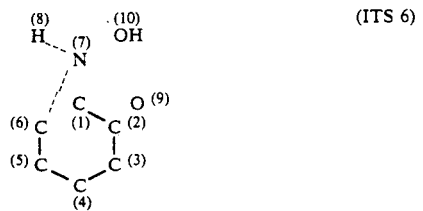 (ITS 6)

ITS 6 was subjected to the operation of extracting ring structure (ITS ring) to obtain a ring structure in the form of character string.

Ring 6a: (1) (6) (7) (1)

A connection table corresponding to ITS 6 is set forth in Table 9.

TABLE 9

| Node No. | King | Coordinate X | Y | Neighbor 1 Node (a, b) | Neighbor 2 Node (a, b) | Neighbor 3 Node (a, b) | Neighbor 4 Node (a, b) |
|---|---|---|---|---|---|---|---|
| 1 | C | 0 | 200 | 2 (1 + 0) | 6 (1 − 1) | 7 (2 − 1) | 9 (0 + 2) |
| 2 | C | 173 | 100 | 1 (1 + 0) | 3 (1 + 0) | | |
| 3 | C | 173 | −100 | 2 (1 + 0) | 4 (1 + 0) | | |
| 4 | C | 0 | −200 | 3 (1 + 0) | 5 (1 + 0) | | |
| 5 | C | −173 | −100 | 4 (1 + 0) | 6 (1 + 0) | | |
| 6 | C | −173 | 100 | 1 (1 − 1) | 5 (1 + 0) | 7 (0 + 1) | |
| 7 | N | 0 | 400 | 1 (2 − 1) | 6 (0 + 1) | 8 (0 + 1) | 10 (1 − 1) |
| 8 | H | −100 | 573 | 7 (0 + 1) | | | |
| 9 | O | 173 | 300 | 1 (0 + 2) | | | |
| 10 | OH | 100 | 573 | 7 (1 − 1) | | | |

The connection table was also subjected to the operation of ITS ring extraction to obtain a connection table of Ring 6a. The result is set forth in Table 10.

TABLE 10

| Bond | (a, b) | a + b | a ≠ 0 a + b ≠ 0 | a + b = 0 | a = 0 |
|---|---|---|---|---|---|
| (1) (6) | (1 − 1) | 0 | — | 1 | — |
| (6) (7) | (0 + 1) | 1 | — | — | 1 |
| (7) (1) | (2 − 1) | 1 | 1 | — | — |

TABLE 10-continued

| Bond | (a, b) | a + b | a ≠ 0 a + b ≠ 0 | a + b = 0 | a = 0 |
|---|---|---|---|---|---|
| Total | | | 1 | 1 | 1 |

It was evident from Table 10 that Ring 6a was a bridge of rearrangement.

Based on the connection table of ITS, two further ring structures were obtained.

Ring 6b: (1) (2) (3) (4) (5) (6) (1)
Ring 6c: (1) (2) (3) (4) (5) (6) (7) (1)

Connection tables of Rings 6b and 6c are respectively set forth in Tables 11 and 12.

TABLE 11

| Bond | (a, b) | a + b | a ≠ 0 a + b ≠ 0 | a + b = 0 | a = 0 |
|---|---|---|---|---|---|
| (1) (2) | (1 + 0) | 1 | 1 | — | — |
| (2) (3) | (1 + 0) | 1 | 1 | — | — |
| (3) (4) | (1 + 0) | 1 | 1 | — | — |
| (4) (5) | (1 + 0) | 1 | 1 | — | — |
| (5) (6) | (1 + 0) | 1 | 1 | — | — |
| (6) (1) | (1 − 1) | 0 | — | 1 | — |
| Total | | | 5 | 1 | 0 |

TABLE 12

| Bond | (a, b) | a + b | a ≠ 0 a + b ≠ 0 | a + b = 0 | a = 0 |
|---|---|---|---|---|---|
| (1) (2) | (1 + 0) | 1 | 1 | — | — |
| (2) (3) | (1 + 0) | 1 | 1 | — | — |
| (3) (4) | (1 + 0) | 1 | 1 | — | — |
| (4) (5) | (1 + 0) | 1 | 1 | — | — |
| (5) (6) | (1 + 0) | 1 | 1 | — | — |
| (6) (7) | (0 + 1) | 1 | — | — | 1 |
| (7) (1) | (2 − 1) | 1 | 1 | — | — |
| Total | | | 6 | 0 | 1 |

It was evident from Table 11 and 12 that Ring 6b is a bridge of ring openings and Ring 6c is a bridge of ring closure. Rings 6a to 6c allowed to express the characteristics of the Beckmann rearrangement that a six-membered ring is opened while a seven-membered ring is produced by the intramolecular rearrangement.

EXAMPLE 2

Methylation Reaction of Cycloheptanone

The reaction is represented by the schematic equation.

A connection table corresponding to ITS 7 is set forth in Table 13.

TABLE 13

| Node No. | Kind | Coordinate X | Y | Neighbor 1 Node (a, b) | Neighbor 2 Node (a, b) | Neighbor 3 Node (a, b) | Neighbor 4 Node (a, b) | Neighbor 5 Node (a, b) |
|---|---|---|---|---|---|---|---|---|
| 1 | C | 0 | 200 | 2 (2 − 1) | 7 (1 + 0) | 8 (1 + 0) | 15 (0 + 1) | |
| 2 | C | 173 | 100 | 1 (2 − 1) | 3 (1 + 0) | 15 (0 + 1) | | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (1 + 0) | 9 (1 + 0) | | | |
| 9 | Si | 0 | 600 | 8 (1 + 0) | 11 (1 + 0) | 12 (1 + 0) | 13 (1 + 0) | |
| 10 | Cl | 0 | 800 | | | | | |
| 11 | CH$_3$ | 100 | 773 | 9 (1 + 0) | | | | |
| 12 | CH$_3$ | 173 | 700 | 9 (1 + 0) | | | | |
| 13 | CH$_3$ | 200 | 600 | 9 (1 + 0) | | | | |
| 14 | H | 314 | −41 | | | | | |
| 15 | CH$_2$ | 200 | 200 | 1 (0 + 1) | 2 (0 + 1) | 16 (1 − 1) | 17 (1 − 1) | |
| 16 | I | 373 | 300 | 15 (1 − 1) | 18 (0 + 1) | | | |
| 17 | I | 373 | 100 | 15 (1 − 1) | 18 (0 + 1) | | | |
| 18 | Zn | 546 | 200 | 16 (0 + 1) | 17 (0 + 1) | | | |

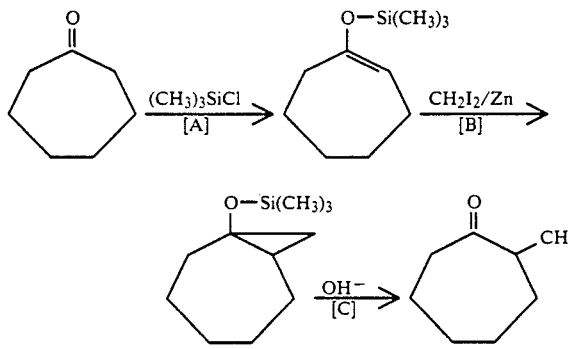

(Eq. 7)

(1) The reaction at step [B] is denoted by the following imaginary transition structure.

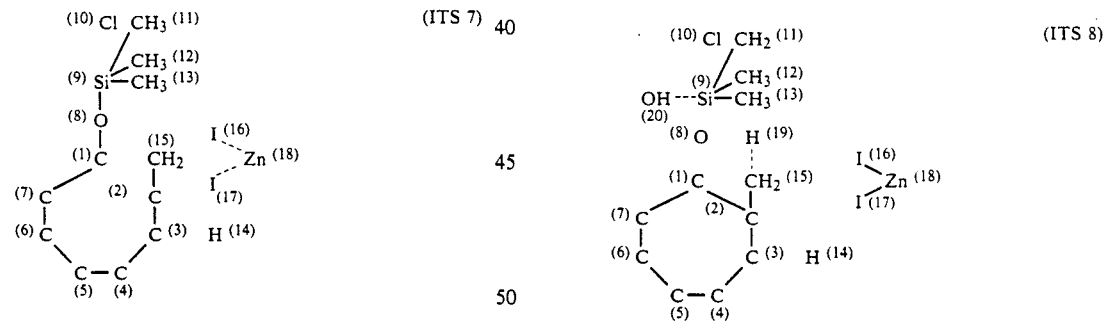

(ITS 7)

ITS 7 was subjected to the operation of ITS ring extraction to obtain a ring structure in the form of character string.

Ring 7: (1) (2) (15) (1)

The connection table was also subjected to the operation of ITS ring extraction to obtain a connection table of Ring 7. The result is set fort in Table 14.

TABLE 14

| Bond | (a, b) | a + b | a ≠ 0 a + b ≠ 0 | a + b = 0 | a = 0 |
|---|---|---|---|---|---|
| (1) (2) | (2 − 1) | 1 | 1 | — | — |
| (2) (15) | (0 + 1) | 1 | — | — | 1 |
| (15) (1) | (0 + 1) | 1 | — | — | 1 |
| Total | | | 1 | 0 | 2 |

It was evident from Table 14 that Ring 7 was a bridge of ring formation.

(2) The reaction at step [C] is denoted by the following imaginary transition structure.

(ITS 8)

ITS 8 was subjected to the operation of ITS ring extraction to obtain a ring structure in the form of character string.

Ring 8: (1) (2) (15) (1)

A connection table corresponding to ITS 8 is set forth in Table 15.

TABLE 15

| Node No. | Kind | Coordinate X | Y | Neighbor 1 Node (a, b) | Neighbor 2 Node (a, b) | Neighbor 3 Node (a, b) | Neighbor 4 Node (a, b) | Neighbor 5 Node (a, b) |
|---|---|---|---|---|---|---|---|---|
| 1 | C | 0 | 200 | 2 (1 + 0) | 7 (1 + 0) | 8 (1 + 1) | 15 (1 − 1) | |
| 2 | C | 173 | 100 | 1 (1 + 0) | 3 (1 + 0) | 15 (1 + 0) | | |
| 3 | C | 173 | −100 | 2 (1 + 0) | 4 (1 + 0) | | | |
| 4 | C | 100 | −286 | 3 (1 + 0) | 5 (1 + 0) | | | |
| 5 | C | −100 | −286 | 4 (1 + 0) | 6 (1 + 0) | | | |
| 6 | C | −173 | −100 | 5 (1 + 0) | 7 (1 + 0) | | | |
| 7 | C | −173 | 100 | 1 (1 + 0) | 6 (1 + 0) | | | |
| 8 | O | 0 | 400 | 1 (1 + 0) | 9 (1 − 1) | | | |

TABLE 15-continued

| Node | | Coordinate | | Neighbor 1 | Neighbor 2 | Neighbor 3 | Neighbor 4 | Neighbor 5 |
|---|---|---|---|---|---|---|---|---|
| No. | Kind | X | Y | Node (a, b) | Node (a, b) | Node (a, b) | Node (a, b) | Node (a, b) |
| 9 | Si | 0 | 600 | 8 (1 − 1) | 11 (1 + 0) | 12 (1 + 0) | 13 (1 + 0) | 20 (0 + 1) |
| 10 | Cl | 0 | 800 | | | | | |
| 11 | CH$_3$ | 100 | 773 | 9 (1 + 0) | | | | |
| 12 | CH$_3$ | 173 | 700 | 9 (1 + 0) | | | | |
| 13 | CH$_3$ | 200 | 600 | 9 (1 + 0) | | | | |
| 14 | H | 314 | −41 | | | | | |
| 15 | CH$_2$ | 200 | 200 | 1 (1 − 1) | 2 (1 + 0) | 19 (0 + 1) | | |
| 16 | I | 373 | 300 | 18 (1 + 0) | | | | |
| 17 | I | 373 | 100 | 18 (1 + 0) | | | | |
| 18 | Zn | 546 | 200 | 16 (1 + 0) | 17 (1 + 0) | | | |
| 19 | H | 200 | 400 | 15 (0 + 1) | | | | |
| 20 | OH | −200 | 600 | 9 (0 + 1) | | | | |

The connection table was also subjected to the operation of ITS ring extraction to obtain a connection table of Ring 8. The result is set forth in Table 16.

TABLE 16

| Bond | (a, b) | a + b | a ≠ 0 a + b ≠ 0 | a + b = 0 | a = 0 |
|---|---|---|---|---|---|
| (1) (2) | (1 + 0) | 1 | 1 | — | — |
| (2) (15) | (1 + 0) | 1 | 1 | — | — |
| (15) (1) | (1 − 1) | 0 | — | 1 | — |
| Total | | 2 | | 1 | 0 |

It was evident from Table 16 that Ring 8 was a bridge of ring opening.

EXAMPLE 3

Epoxidation Reaction of Halohydrin

The reaction is represented by the schematic equation.

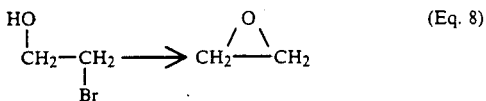 (Eq. 8)

The epoxidation reaction is denoted by the following imaginary transition structure.

 (ITS 9)

ITS 9 was subjected to the operation of ITS ring extraction to obtain a ring structure in the form of character string.

Ring 9: (1) (2) (3) (1)

A connection table corresponding to ITS 9 is set forth in Table 17.

TABLE 17

| Node | | Coordinate | | Neighbor 1 | Neighbor 2 | Neighbor 3 | Neighbor 4 |
|---|---|---|---|---|---|---|---|
| No. | King | X | Y | Node (a, b) | Node (a, b) | Node (a, b) | Node (a, b) |
| 1 | CH$_2$ | 0 | 0 | 2 (1 + 0) | 3 (1 + 0) | | |
| 2 | CH$_2$ | 200 | 0 | 1 (1 + 0) | 3 (0 + 1) | 5 (1 − 1) | |
| 3 | O | 100 | 200 | 1 (1 + 0) | 2 (0 + 1) | 4 (1 − 1) | |
| 4 | H | 0 | 250 | 3 (1 − 1) | | | |
| 5 | Br | 200 | −200 | 2 (1 − 1) | | | |

The connection table was also subjected to the operation of ITS ring extraction to obtain a connection table of Ring 9. The result is set forth in Table 18.

TABLE 18

| Bond | (a, b) | a + b | a ≠ 0 a + b ≠ 0 | a + b = 0 | a = 0 |
|---|---|---|---|---|---|
| (1) (2) | (1 + 0) | 1 | 1 | — | — |
| (2) (3) | (0 + 1) | 1 | — | — | 1 |
| (3) (1) | (1 + 0) | 1 | 1 | — | — |
| Total | | 2 | 0 | | 1 |

It was evident from Table 18 that Ring 9 was a bridge of ring closure.

I claim:

1. A method of storing information for an organic chemical reaction in which a reaction of at least one starting material to give at least one reaction product is involved; which comprises the steps:

(a) topologically superposing a chemical structural formula of the starting material or a combination of chemical structural formulae of the starting materials on a chemical structural formula of the reaction product or a combination of chemical structural formulae of the reaction products to give an imaginary transition structure;

(b) classifying each bond linking two nodes of the imaginary transition structure into the following three groups; (1) bond linking two nodes appearing both in the formulae of the starting material and the reaction product, (2) bond linking two nodes appearing only in the formula of the starting material, and (3) bond linking two nodes appearing only in the formula of the reaction product;

(c) representing nodes and bonds classified in step (b) in the form of a connection table;

(d) detecting ring structures in the connection table;

(e) classifying the ring structures into any type of the following five groups; (I) ring structure which contains one bond of (2) and does not contain the bond of (3), (II) ring structure which contains two or more bonds of (2) and does not contain the bond of (3); (III) ring structure which does not contain the bond of (2) and contains one bond of (3); (IV) ring structure which does not contain the bond of (2) and contains two or more bonds of (3); and (V)

ring structure which contains one bond of (2) and one bond of (3); and (f) storing the classified ring structures in a recording material.

2. The method of claim 1, wherein the step of classifying each bond is performed by denoting the bond linking two nodes in the connection table using pairs of integers:

(1+0) which denotes a bond having one bond of (1) only;

(2+0) which denotes a bond having two bonds of (1) only;

(3+0) which denotes a bond having three bonds of (1) only;

(1−1) which denotes a bond having one bond of (2) only;

(2−1) which denotes a bond having one bond of (1) and one bond of (2) only;

(3−1) which denotes a bond having two bonds of (1) and one bond of (2) only;

(2−2) which denotes a bond having two bonds of (2) only;

(3−2) which denotes a bond having one bond of one and two bonds of (2) only;

(3−3) which denotes a bond having three bonds of (2) only;

(0+1) which denotes a bond having one bond of (3) only;

(1+1) which denotes a bond having one bond of (1) and one bond of (3) only;

(2+1) which denotes a bond having two bonds of (1) and one bond of (3) only;

(0+2) which denotes a bond having two bonds of (3) only;

(1+2) which denotes a bond having one bond of (1) and two bonds of (3) only; and (0+3) which denotes a bond having three bonds of (3) only.

3. A method of storing information for an organic reaction in which a reaction of at least one starting material to give at least one reaction product is involved; which comprises the steps:

(a) topologically superposing a chemical structural formula of the starting material or a combination of chemical structural formulae of the starting materials on a chemical structural formula of the reaction product or a combination of chemical structural formulae of the reaction products to give an imaginary transition structure;

(b) classifying each bond linking two nodes of the imaginary transition structure into the following three groups; (1) bond linking two nodes appearing both in the formulae of the starting material and the reaction product, (2) bond linking two nodes appearing only in the formula of the starting material, and (3) bond linking two nodes appearing only in the formula of the reaction product;

(c) representing nodes and bonds classified in step (b) in the form of a connection table;

(d) extracting from the connection table information on at least one ring structure composed of plural bonds of (1) and one bond of (2); and (e) storing the information on the ring structure in a recording material.

4. The method of claim 3, wherein the step of classifying each bond is performed by denoting the bond linking two nodes in the connection table using pairs of integers:

(1+0) which denotes a bond having one bond of (1) only;

(2+0) which denotes a bond having two bonds of (1) only;

(3+0) which denotes a bond having three bonds of (1) only;

(1−1) which denotes a bond having one bond of (2) only;

(2−1) which denotes a bond having one bond of (1) and one bond of (2) only;

(3−1) which denotes a bond having two bonds of (1) and one bond of (2) only;

(2−2) which denotes a bond having two bonds of (2) only;

(3−2) which denotes a bond having one bond of one and two bonds of (2) only;

(3−3) which denotes a bond having three bonds of (2) only;

(0+1) which denotes a bond having one bond of (3) only;

(1+1) which denotes a bond having one bond of (1) and one bond of (3) only;

(2+1) which denotes a bond having two bonds of (1) and one bond of (3) only;

(0+2) which denotes a bond having two bonds of (3) only;

(1+2) which denotes a bond having one bond of (1) and two bonds of (3) only; and (0+3) which denotes a bond having three bonds of (3) only.

5. A method of storing information for an organic reaction in which a reaction of at least one starting material to give at least one reaction product is involved; which comprises the steps:

(a) topologically superposing a chemical structural formula of the starting material or a combination of chemical structural formula of the starting materials on a chemical structural formula of the reaction product or a combination of chemical structural formulae of the reaction products to give an imaginary transition structure;

(b) classifying each bond linking two nodes of the imaginary transition structure into the following three groups; (1) bond linking two nodes appearing both in the formulae of the starting material and the reaction product, (2) bond linking two nodes appearing only in the formula of the starting material, and (3) bond linking two nodes appearing only in the formula of the reaction product;

(c) representing nodes and bonds classified in step (b) in the form of a connection table;

(d) extracting from the connection table information on at least one ring structure composed of one or more bonds of (1) and two or more bonds of (2); and (e) storing the information on the ring structure in a recording material.

6. The method of claim 5, wherein the step of classifying each bond is performed by denoting the bond linking two nodes in the connection table using pairs of integers:

(1+0) which denotes a bond having one bond of (1) only;

(2+0) which denotes a bond having two bonds of (1) only;

(3+0) which denotes a bond having three bonds of (1) only;

(1−1) which denotes a bond having one bond of (2) only;

(2−1) which denotes a bond having one bond of (1) and one bond of (2) only;

(3−1) which denotes a bond having two bonds of (1) and one bond of (2) only;

(2−2) which denotes a bond having two bonds of (2) only;

(3−2) which denotes a bond having one bond of one and two bonds of (2) only;

(3−3) which denotes a bond having three bonds of (2) only;

(0+1) which denotes a bond having one bond of (3) only;

(1+1) which denotes a bond having one bond of (1) and one bond of (3) only;

(2+1) which denotes a bond having two bonds of (1) and one bond of (3) only;

(0+2) which denotes a bond having two bonds of (3) only;

(1+2) which denotes a bond having one bond of (1) and two bonds of (3) only; and (0+3) which denotes a bond having three bonds of (3) only.

7. A method of storing information for an organic reaction in which a reaction of at least one starting material to give at least one reaction product is involved; which comprises the steps:
   (a) topologically superposing a chemical structural formula of the starting material or a combination of chemical structural formulae of the starting materials on a chemical structural formula of the reaction product or a combination of chemical structural formulae of the reaction products to give an imaginary transition structure;
   (b) classifying each bond linking two nodes of the imaginary transition structure into the following three groups; (1) bond linking two nodes appearing both in the formulae of the starting material and the reaction product, (2) bond linking two nodes appearing only in the formula of the starting material, and (3) bond linking two nodes appearing only in the formula of the reaction product;
   (c) representing nodes and bonds classified in step (b) in the form of a connection table;
   (d) extracting from the connection table information on at least one ring structure composed of plural bonds of (1) and one bond of (3); and
   (e) storing the information on the ring structure in a recording material.

8. The method of claim 7, wherein the step of classifying each bond is performed by denoting the bond linking two nodes in the connection table using pairs of integers:

(1+0) which denotes a bond having one bond of (1) only;

(2+0) which denotes a bond having two bonds of (1) only;

(3+0) which denotes a bond having three bonds of (1) only;

(1−1) which denotes a bond having one bond of (2) only;

(2−1) which denotes a bond having one bond of (1) and one bond of (2) only;

(3−1) which denotes a bond having two bonds of (1) and one bond of (2) only;

(2−2) which denotes a bond having two bonds of (2) only;

(3−2) which denotes a bond having one bond of one and two bonds of (2) only;

(3−3) which denotes a bond having three bonds of (2) only;

(0+1) which denotes a bond having one bond of (3) only;

(1+1) which denotes a bond having one bond of (1) and one bond of (3) only;

(2+1) which denotes a bond having two bonds of (1) and one bond of (3) only;

(0+2) which denotes a bond having two bonds of (3) only;

(1+2) which denotes a bond having one bond of (1) and two bonds of (3) only; and (0+3) which denotes a bond having three bonds of (3) only.

9. A method of storing information for an organic reaction in which a reaction of at least one starting material to give at least one reaction product is involved; which comprises the steps:
   (a) topologically superposing a chemical structural formula of the starting material or a combination of chemical structural formulae of the starting materials on a chemical structural formula of the reaction product or a combination of chemical structural formulae of the reaction products to give an imaginary transition structure;
   (b) classifying each bond linking two nodes of the imaginary transition structure into the following three groups; (1) bond linking two nodes appearing both in the formulae of the starting material and the reaction product, (2) bond linking two nodes appearing only in the formula of the starting material, and (3) bond linking two nodes appearing only in the formula of the reaction product;
   (c) representing nodes and bonds classified in step (b) in the form of a connection table;
   (d) extracting from the connection table information on at least one ring structure composed of one or more bonds of (1) and two or more bonds of (3); and
   (e) storing the information on the ring structure in a recording material.

10. The method of claim 9, wherein the step of classifying each bond is performed by denoting the bond linking two nodes in the connection table using pairs of integers:

(1+0) which denotes a bond having one bond of (1) only;

(2+0) which denotes a bond having two bonds of (1) only;

(3+0) which denotes a bond having three bonds of (1) only;

(1−1) which denotes a bond having one bond of (2) only;

(2−1) which denotes a bond having one bond of (1) and one bond of (2) only;

(3−1) which denotes a bond having two bonds of (1) and one bond of (2) only;

(2−2) which denotes a bond having two bonds of (2) only;

(3−2) which denotes a bond having one bond of one and two bonds of (2) only;

(3−3) which denotes a bond having three bonds of (2) only;

(0+1) which denotes a bond having one bond of (3) only;

(1+1) which denotes a bond having one bond of (1) and one bond of (3) only;

(2+1) which denotes a bond having two bonds of (1) and one bond of (3) only;

(0+2) which denotes a bond having two bonds of (3) only;

(1+2) which denotes a bond having one bond of (1) and two bonds of (3) only; and (0+3) which denotes a bond having three bonds of (3) only.

11. A method of storing information for an organic reaction in which a reaction of at least one starting material to give at least one reaction product is involved; which comprises the steps:

(a) topologically superposing a chemical structural formula of the starting material or a combination of chemical structural formulae of the starting materials on a chemical structural formula of the reaction product or a combination of chemical structural formulae of the reaction products to give an imaginary transition structure;

(b) classifying each bond linking two nodes of the imaginary transition structure into the following three groups; (1) bond linking two nodes appearing both in the formulae of the starting material and the reaction product, (2) bond linking two nodes appearing only in the formula of the starting material, and (3) bond linking two nodes appearing only in the formula of the reaction product;

(c) representing nodes and bonds classified in step (b) in the form of a connection table;

(d) extracting from the connection table information on at least one ring structure composed of one or more bonds of (1), one bond of (2) and one bond of (3); and (e) storing the information on the ring structure in a recording material.

12. The method of claim 9, wherein the step of classifying each bond is performed by denoting the bond linking two nodes in the connection table using pairs of integers:

(1+0) which denotes a bond having one bond of (1) only;

(2+0) which denotes a bond having two bonds of (1) only;

(3+0) which denotes a bond having three bonds of (1) only;

(1−1) which denotes a bond having one bond of (2) only;

(2−1) which denotes a bond having one bond of (1) and one bond of (2) only;

(3−1) which denotes a bond having two bonds of (1) and one bond of (2) only;

(2−2) which denotes a bond having two bonds of (2) only;

(3−2) which denotes a bond having one bond of one and two bonds of (2) only;

(3−3) which denotes a bond having three bonds of (2) only;

(0+1) which denotes a bond having one bond of (3) only;

(1+1) which denotes a bond having one bond of (1) and one bond of (3) only;

(2+1) which denotes a bond having two bonds of (1) and one bond of (3) only;

(0+2) which denotes a bond having two bonds of (3) only;

(1+2) which denotes a bond having one bond of (1) and two bonds of (3) only; and (0+3) which denotes a bond having three bonds of (3) only.

* * * * *